United States Patent [19]
Müller et al.

[11] Patent Number: 5,658,340
[45] Date of Patent: Aug. 19, 1997

[54] ENDOPROSTHESIS FOR A SHOULDER JOINT

[75] Inventors: Holger Müller, Gettorf, Germany; Herbert Ferdinand Resch, Innsbruck, Austria; Bernd Robioneck, Schellhorn, Germany

[73] Assignee: Howmedica GmbH, Schoenkirchen, Germany

[21] Appl. No.: 291,235

[22] Filed: Aug. 16, 1994

[30] Foreign Application Priority Data

Aug. 16, 1993 [DE] Germany ............... 9312218.7 U

[51] Int. Cl.⁶ .................................................. A61F 2/40
[52] U.S. Cl. ........................... 623/19; 623/18; 623/23
[58] Field of Search .............................. 623/19, 23, 18, 623/22

[56] References Cited

U.S. PATENT DOCUMENTS

| | | | |
|---|---|---|---|
| 3,102,536 | 9/1963 | Rose et al. | 623/19 |
| 3,806,957 | 4/1974 | Shersher | 623/19 |
| 4,520,511 | 6/1985 | Gianezio et al. | 623/23 |
| 4,865,605 | 9/1989 | Dine et al. | 623/19 |
| 5,358,524 | 10/1994 | Richelsoph | 623/18 |
| 5,358,526 | 10/1994 | Tornier | 623/19 |

FOREIGN PATENT DOCUMENTS

| | | | |
|---|---|---|---|
| 0309662 | 4/1989 | European Pat. Off. | 623/23 |
| 2349318 | 11/1977 | France. | |
| 2578739 | 9/1986 | France. | |

*Primary Examiner*—John G. Weiss
*Assistant Examiner*—Bruce E. Snow
*Attorney, Agent, or Firm*—Peter C. Richardson; Lawrence C. Akers; Elizabeth O. Slade

[57] ABSTRACT

An endoprosthesis for a shoulder joint that provides for an adjustable distance between the head portion and the shank portion is provided. The head portion of the endoprosthesis is connected through a threaded connection to the proximal end of the shank portion such that the distance between the head portion and the shank portion can be varied. In operation, the head portion is screwed into the shank portion until the desired distance is obtained.

4 Claims, 2 Drawing Sheets

ENDOPROSTHESIS FOR A SHOULDER JOINT

BACKGROUND OF THE INVENTION

The present invention relates to an endoprosthesis for a shoulder joint.

An endoprosthesis of this type usually includes a tapered plug-in connection between a head portion including a spherical joint surface and an elongate shank portion. The axis of the plug-in connection coincides with the axis of the shank and the center of curvature of the joint surface is spaced from that axis.

For this structure the distance between the joint surface (i.e., the center of curvature thereof) and the shank portion depends on the shape of the head portion and cannot be varied any more after the head portion has been manufactured. In particular, the lateral distance of the humerus from the joint cannot be adjusted.

It is an object of the present invention to provide an endoprosthesis for a shoulder joint that provides for an adjustable distance between the head portion and the shank portion.

SUMMARY OF THE INVENTION

According to the invention, the head portion of an endoprosthesis is connected through a threaded connection to the proximal end of the shank portion such that the distance between the head portion and the shank portion can be varied. In the operation the head portion is screwed into the shank portion until the desired distance is obtained.

According to the invention, in one embodiment, the center of curvature of the joint surface is located on the axis of a first threaded portion. This allows the head portion to be symmetrically formed, and this has advantages when the head portion is screwed into the shank portion.

According to the invention, in another embodiment, the axis of a second threaded portion is inclined with respect to the longitudinal axis of the shank portion. This makes it possible to adjust the lateral distance between the joint and the humerus. The angle of inclination is preferably about 50° to conform to the natural joint.

In a still further embodiment of the invention, the first threaded portion is formed as a threaded pin having an outer thread and the second threaded portion is formed as a threaded bore. On the one hand, this facilitates the handling when the head portion is screwed in and, on the other hand, the head portion can be secured against rotation in the shank portion.

In further embodiment of the invention, the threaded pin includes peripherally spaced longitudinal grooves extending parallel to the axis, the grooves preferably including a rounded transverse profile to secure the pin against a rotation.

According to a further embodiment of the invention, the head portion includes reference markings provided at the edge or on the lower side of the joint surface (which markings are aligned to said longitudinal grooves). Thus the surgeon is able to observe the orientation of the longitudinal grooves even when the thread is not visible.

In a further embodiment of the invention, the head portion includes recesses to be engaged by a turning tool to exert high torque (which recesses are located on or close to the edge or at the lower side of the joint surface).

Still further, the longitudinal grooves are each about 90°, and the respective markings are formed as engaging recesses.

According to a further embodiment of the invention, the second thread is formed in a blind bore so that bony material cannot grow into the bore.

According to a still further embodiment of the invention, a locking screw is turned into a threaded bore transversally extending with respect to the second threaded portion. This locking screw can engage a longitudinal groove of the threaded pin to secure the pin against rotation. The locking screw is preferably defined by a pin-type screw, preferably including a rounded tip and a head formed for engagement by a turning tool. According to a preferred embodiment of the invention, the shaft of the locking screw includes a transversally extending plastic insert. The plastic insert prevents an accidental release of the rotary lock.

Still further, the invention provides for a peen having openings proximally attached to the shank portion for mounting fractured parts of the humerus bone.

According to a further embodiment of the invention, the shank portion includes a proximal portion having openings, preferably axially extending elongate openings and a smooth distal portion. The shank portion first entering the humerus comprises a smooth surface, while the openings in the proximal shank portion facilitate an anchoring by means of bony material growing in.

According to a further embodiment of the invention, the shank portion in close proximity to the proximal end of the threaded portion includes a collar extending vertically with respect thereto, and the shank portion includes an oval cross section at the top of the distal end of the threaded portion with reference to the longitudinal axis of the shank. The joining areas between bone, shank and head may be thus designed to be of appropriate shape.

In a further embodiment of the invention, the head portion, the shank portion and/or the locking screw are made of metal, preferably titanium or a cobalt-chrome alloy.

DESCRIPTION OF THE PREFERRED EMBODIMENTS

DETAILED DESCRIPTION OF THE DRAWINGS

Figure 1:
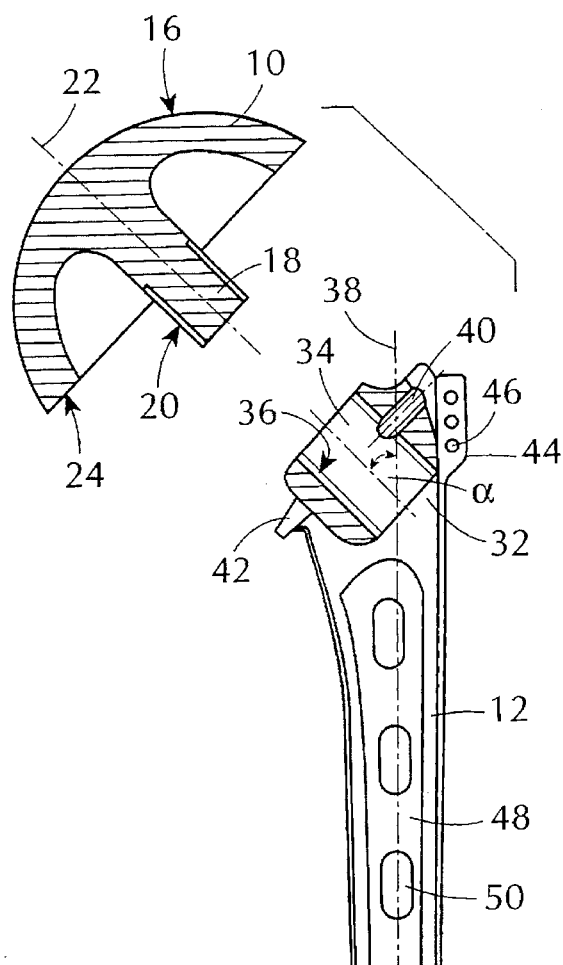
FIG. 1 shows a side view, partly in cross-section, of an endoprosthesis for a shoulder joint according to the invention.
Figure 1A:
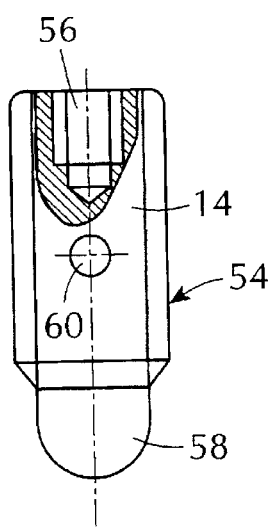
FIG. 1A shows a side view, partly in cross-section of a locking screw for use in FIG. 1.

With reference to FIGS. 1 and 1A, the endoprosthesis for a shoulder joint comprises a head portion 10 which is screwed into a shank portion 12 and which is secured by a locking screw 14. The head portion 10 formed as a rotational head may cooperate with an artificial joint socket (not shown) of a natural shoulder bone (likewise not shown) to define a shoulder joint.

Figure 2:
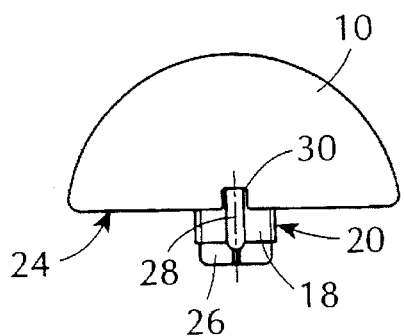
FIG. 2 shows a side view of the head portion of the endoprosthesis of FIG. 1.
Figure 3:
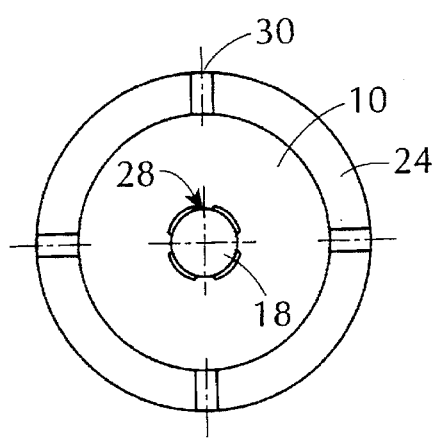
FIG. 3 shows a top view of the head portion of FIG. 2 from the distal end.

The head portion 10 includes a spherically shaped joint surface 16 and a threaded pin 18 including an outer thread 20. The joint surface 16 is approximately hemispherically shaped with the center of curvature being located on the axis 22 of the threaded pin 18. The joint surface 16 terminates in an edge 24. As FIGS. 2 and 3 show in some detail, the outer side 20 of the threaded pin 18 extends up to a recess 26 provided at the free end of the pin 18.

The threaded pin 18 includes four peripherally spaced longitudinal grooves extending parallel to the axis and having a rounded profile. Four markings 30 shaped as engaging recesses are provided along the edge 24 of the joint surface 16, which markers are aligned with longitudinal grooves 28 of the threaded pin 18.

The proximal end of the shank portion 12 includes a threaded portion 32 comprising a bore 34 including an internal thread 36 cooperating with the outer thread 20 along the thread axis 22. The axis 22 is inclined at an angle α with respect to the longitudinal axis 38 of the shank portion 12. The proximal end of the shank 12 further includes a threaded bore 40 extending perpendicular to the axis 22 for receiving a locking screw 14 (shown in FIG. 1A), said shank further comprising a peripheral collar 42 likewise extending perpendicular to the axis 22. Still further a peen 44 having three openings 46 is provided close to the proximal end of the shank.

The shank 12 has a proximal portion 48 (including axially elongate openings 50) and a smooth distal portion 52.

As shown in FIG. 1A, the locking screw 14 is a pin-type screw including an outer thread 54 and a head 56 to be shaped for being engaged by a turning tool, as well as a rounded tip 58. The pin-type screw further includes a bore 60 housing a plastic plaque.

Figure 4:
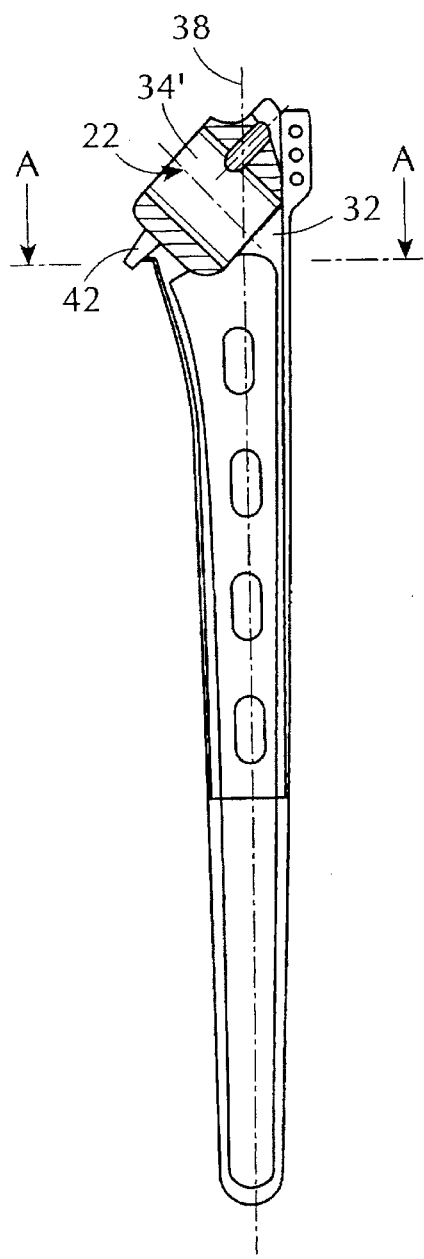
FIG. 4 shows a side view, partly in section, of a shank portion according to the invention.
Figure 5:
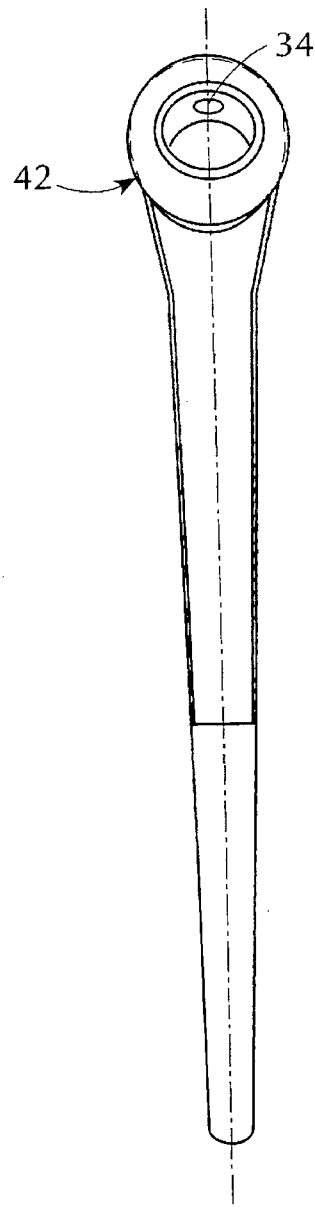
FIG. 5 shows a front view of the shank portion of FIG. 4.
Figure 6:
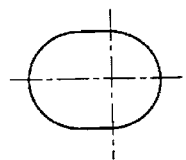
FIG. 6 shows a cross-sectional view of the shank portion of FIG. 4 taken along line A—A.

FIGS. 4 to 6 show an alternative embodiment of the endoprosthesis according to the invention in further detail. The threaded bore 34' cooperating with the threaded pin 18 of the head portion 10 is shaped as a blind bore i.e., a bore which is open only at one end. All the remaining features shown correspond to the embodiment described with reference to FIG. 1.

The concentrical shape of the collar 42 with respect to the axis 22 is clearly visible. FIG. 6 shows the oval cross section of the shank with respect to the axis 38 in a section A—A in the height of the distal end of the threaded portion 32.

In operation, the shank portion with the smooth distal portion 52 being directed forwardly is driven into the humerus. The head portion 10 is guided along the axis 22 towards the shank portion 12, and is screwed with the threaded pin 18 into the threaded bore 34 until the desired distance between the joint surface 16 and the shank portion 12 with respect to its axis 38, for example, is obtained. The next mark (i.e., engaging recess 30) will be aligned to the bore 40 and the locking screw 14 including the plastic insert will be fixed in the threaded bore 40. The pin-type screw 14 is tightened until its rounded tip 58 engages in the longitudinal groove 28 of the threaded pin 18. The head 10 is then locked against a rotary motion about the axis 22, while the plastic insert of the screw prevents loosening. Now the endoprosthesis including the joint surface 16 may be inserted in the bone (not shown) and fractured parts, if any, may be secured to the peen 44. After inserting the prosthesis without cement, bony material will grow into the elongate openings 50 of the proximal shank portion 48.

What is claimed is:

1. An endoprosthesis for a shoulder joint, comprising a head portion (10) including a hemispherical joint surface (16) and an elongate shank portion (12) which is to be driven into the proximal humerus and which is to be connected to said head portion (10), wherein the head portion (10) includes a first threaded portion (18) cooperating with a second threaded portion (34) provided at the proximal end (32) of the shank portion (12) such that the distance between the head portion and the shank portion is adjustable, wherein said first threaded portion 18 has an axis (22) which extends approximately through the center of curvature of said spherical joint surface (16), wherein said second threaded portion (34) has an axis which coincides with said axis (22), wherein said shank portion (12) has a longitudinal axis (38), and wherein said axis (22) is inclined at an angle of about 50° with respect to said longitudinal axis (38) of said shank portion (12), wherein the first threaded portion (18) is a threaded pin including an outer thread (20), wherein the second threaded portion (34) is a threaded bore, wherein the threaded pin (18) includes longitudinal grooves extending parallel to said axis (22) and are peripherally spaced, said grooves being engaged by a locking means (14) for non-rotatably securing said pin, wherein said longitudinal grooves (28) include a rounded cross-sectional profile, and wherein said head portion includes reference marks (30) which are alignable with said longitudinal grooves.

2. The endoprosthesis of claim 1, wherein said head portion includes recesses having sides which are substantially parallel axially extending walls for engagement with a turning tool.

3. The endoprosthesis of claim 2, wherein four longitudinal grooves are provided peripherally spaced at intervals of 90° and wherein said reference marks (30) are formed as recesses having sides which are substantially parallel axially extending walls.

4. The endoprosthesis of claim 3, wherein said second thread is formed in a blind bore which is open only at one end.

* * * * *